United States Patent [19]

Craig et al.

[11] Patent Number: Plant 6,654

[45] Date of Patent: Mar. 7, 1989

[54] GERANIUM PLANT '#854-(82-114-7) JULIET'

[75] Inventors: Richard Craig; Leon Glicenstein, both of State College, Pa.

[73] Assignee: Research Corporation Technologies, Inc., Tucson, Ariz.

[21] Appl. No.: 75,012

[22] Filed: Jul. 17, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Scully, Scott, Murphy & Presser

[57] ABSTRACT

This invention relates to a new distinct cultivar of geranium substantially as illustrated and described, characterized as being particularly well adapted to both commercial greenhouse production as well as garden performance, and as being early, floriferous, self-branching, compact, heat-tolerant and low-light-tolerant.

2 Drawing Sheets

1

The present invention relates to a new and distinct cultivar of geranium *Pelargonium*×*hortorum* called '#854-(82-114-7)' and is given the variety name, Juliet. The cultivar is particularly well adapted to both commercial greenhouse production and garden performance. The cultivar is characterized as to novelty as being early, floriferous, self-branching and compact.

The cultivar was developed from an organized, scientifically designed breeding program carried out at the Department of Horticulture, The Pennsylvania State University, University Park, Pa. 16802. The breeding program was designed to create new geranium genotypes with clear, bright colors which combined the flowering ability and compactness of European cultivars with the heat tolerance, low light tolerance and excellent greenhouse production qualities of native cultivars. The pedigree of this cultivar is as follows:

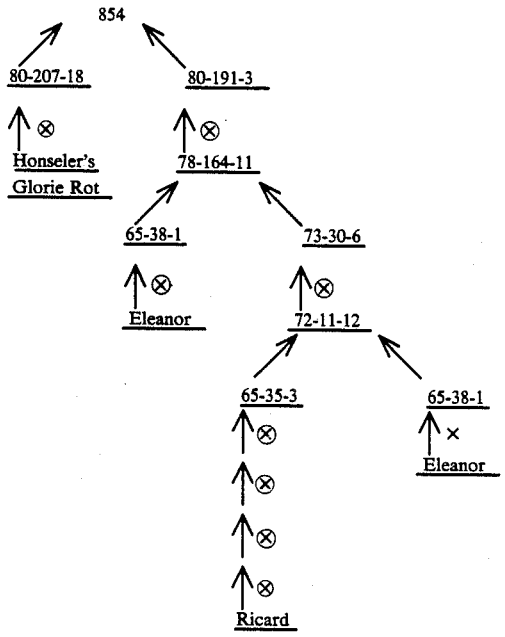

The selection was asexually propagated by cuttings and the reproductions ran true.

2

Figure 1:
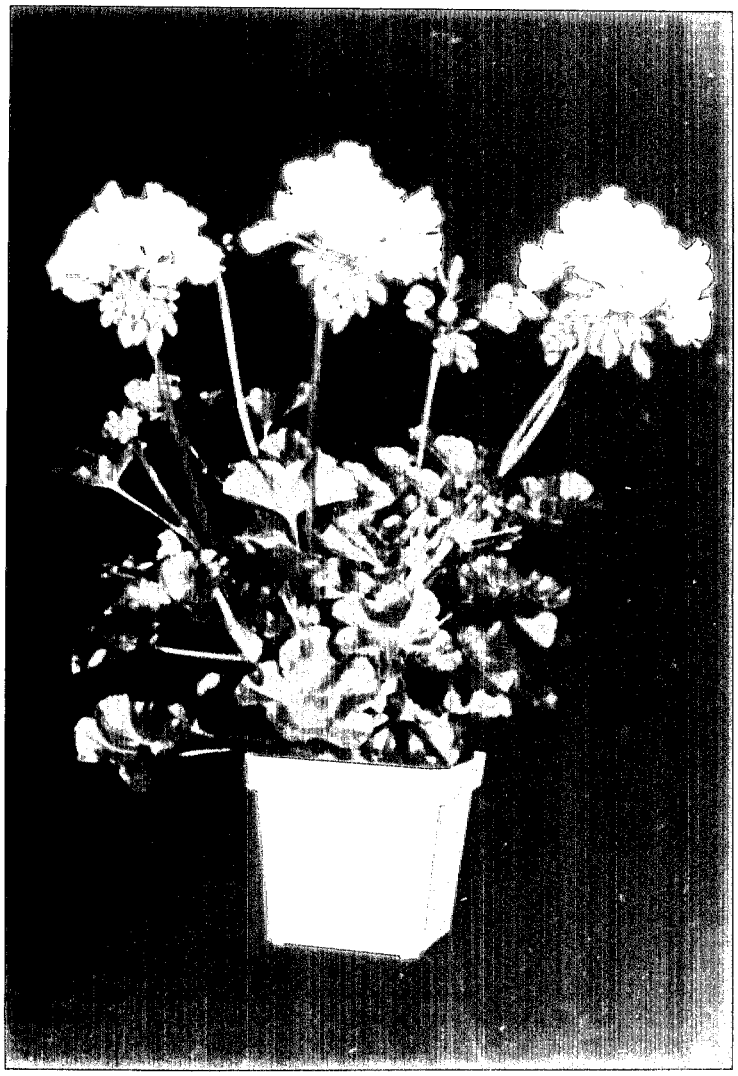
FIG. 1 illustrates in color the cultivar including foliage and flowers.
Figure 2:
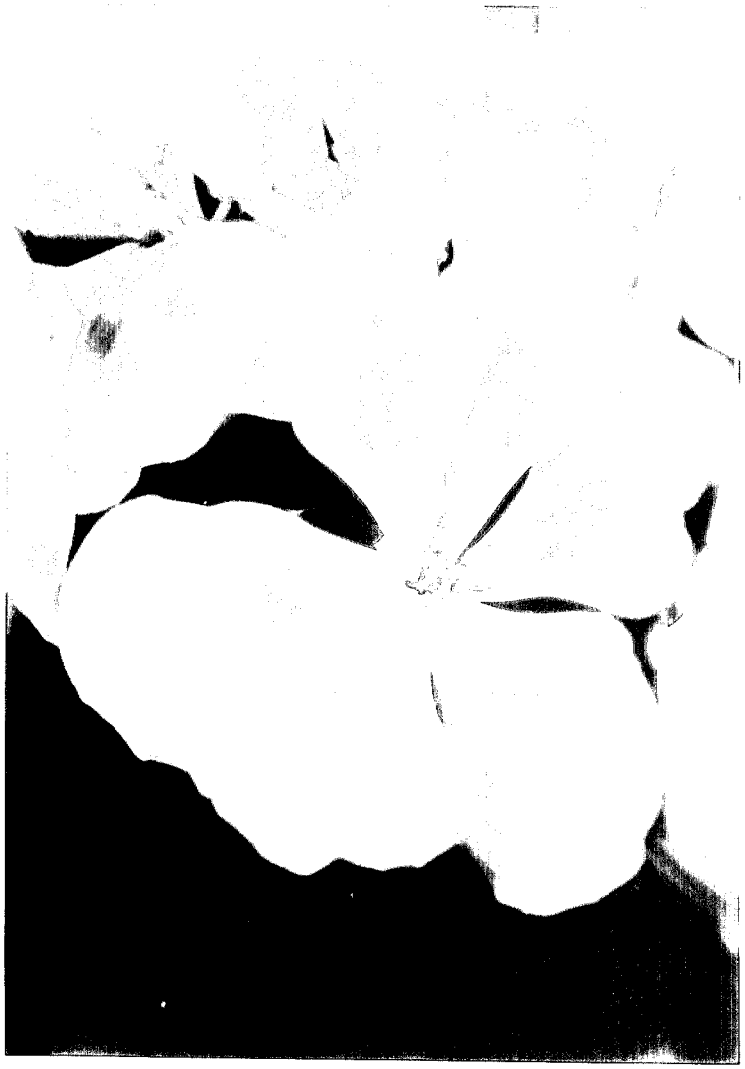
FIG. 2 illustrates in color primarily the floret.

With reference to the detailed description of the cultivar which follows, the test plant was grown in a glasshouse under full natural light, at a minimum night temperature of 58° F., and a minimum day temperature of 68° F. Soilless medium was fertilized constantly with 200 ppm N as 15-16-17. Color readings were taken under incandescent light at 200 foot candles and color identification was by reference to The Royal Horticultural Society Colour Charts, except where common terms of color definition are employed.

THE PLANT

Classification:

*Botanical.*—*Pelargonium*×*hortorum.*

*Tradename.*—#854-(82-114-7).

Form: Compact, self-branching.

Height: Average: 21.0 cm; range 17.0–26.0 cm.

Growth: Free branching from base; short internodes; stands upright with no artificial support.

Leaves:

*Size.*—Largest measured 5.5 cm long×10.0 cm wide; ratio of length to width approximately 2:3.

*Shape.*—Reniform, variously lobed.

*Margin.*—Crenate.

*Texture.*—Pubescent; dull.

*Color.*—Adaxial: Distal: Green group 137B. Proximal: Green group 137C. Abaxial: Green group 138B.

*Ribs and veins.*—Palmate venation; veins recessed and prominent.

*Petioles.*—Lightly pubescent. Length: Up to 10.2 cm. Color: Green group 138B.

Stem:

*Internode length.*—Up to 2.0 cm.

*Color.*—Green group 138B.

THE FLOWER

Blooming habit: Continuous.

Inflorescence form: Umbel.

Inflorescence size: Depends on number of florets; inflorescence often 9.5 cm across or larger.

Persistence: Persistent, non-shattering.

Disease resistance: Not known; favorable in outdoor trails.

Lasting quality: Excellent; usually 3 weeks or longer.

Florets:

*Number.*—Often over 50 inflorescence.

*Form.*—Flat to cupped.

*Size.*—2.5–3.7 cm across open floret.

*Petals.*—Number: 5–7. Texture and appearance: Smooth to slightly wrinkled. Color: Upper petal: Adaxial: Red group 57C with *central spot* red-purple group 57A and base white group 155D with streaks red-purple group 66A. Abaxial: Red-purple group 62B. Lower petal: Adaxial: Red group 57D with *central spot* red group 57A and *base* white group 155D. Abaxial: Red-purple group 62B.

*Petaloids.*—Number: 1. Shape: Variable; often misshapen. Color: Petal-like. Sepals: Number: 5–7. Pedicel: Length: 1.1–1.8 cm. Color: Green group 138B.

Peduncle: Arises from node; opposed to leaf petiole; thick (up to 5 mm diameter).

*Length.*—7.0–12.0 cm.

*Color.*—Green group 138B.

Reproductive Organs

Androecium:

*Stamens.*—Up to 10 flat, ribbon-like white filaments with purple tips, joined at their bases; versatile attachment to anthers which are purple and well developed; orange pollen.

*Staminodes.*—None observed.

*Petaloid stamens.*—At least 1 petal-like filment with a partially developed anther.

Gynoecium:

*Pistil number.*—1. Length: 6.0–10.0 mm. Stigma: 5–7-parted. Style: 1.0 mm long; green. Ovary: 5–7-parted; superior; pubescent.

*Fruit.*—Achene schizocarp; rarely observed.

What is claimed is:

1. A new distinct cultivar of geranium substantially as illustrated and described, characterized as being particularly well adapted to both commercial greenhouse production as well as garden performance, and as being early, floriferous, self-branching, compact, heat-tolerant and low-light-tolerant.

* * * * *

UNITED STATES PATENT AND TRADEMARK OFFICE

CERTIFICATE OF CORRECTION

PATENT NO. : Plant 6,654

DATED : March 7, 1989

INVENTOR(S) : Richard Craig, et al.

It is certified that error appears in the above-identified patent and that said Letters Patent is hereby corrected as shown below:

Column 3, line 19: "1.1" should read as --1.4--

Signed and Sealed this

Thirtieth Day of January, 1990

*Attest:*

JEFFREY M. SAMUELS

*Attesting Officer*

*Acting Commissioner of Patents and Trademarks*